United States Patent [19]
Gillespie et al.

[11] Patent Number: 4,703,049
[45] Date of Patent: Oct. 27, 1987

[54] 2-(1,2,4-OXADIAZOL-5-YL) AND 2-(1,3,4-THIADIAZOL-2-YL-IMIDAZO[1,2-A]PYRIMIDINES

[75] Inventors: Roger J. Gillespie, Swindon; Wilfred R. Tully, Cirencester, both of England

[73] Assignee: Roussel Uclaf, Paris, France

[21] Appl. No.: 808,844

[22] Filed: Dec. 12, 1985

[30] Foreign Application Priority Data

Dec. 19, 1984 [GB] United Kingdom ............... 8432073

[51] Int. Cl.$^4$ .................. A61K 31/415; C07D 235/02
[52] U.S. Cl. ................................. 514/258; 514/267; 544/281; 544/250
[58] Field of Search ............... 544/281, 250; 514/258, 514/267

[56] References Cited

U.S. PATENT DOCUMENTS 4,588,720 5/1986 Tully et al. .................... 544/281

FOREIGN PATENT DOCUMENTS 0120589 8/1984 European Pat. Off. ........... 544/281

Primary Examiner—Donald G. Daus
Assistant Examiner—Barbara Cassatt
Attorney, Agent, or Firm—Bierman & Muserlian

[57] ABSTRACT

Novel compounds selected from the group consisting of the formula

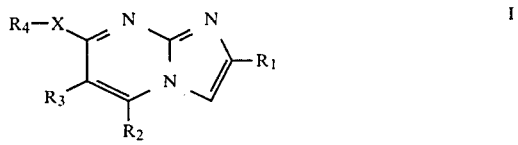

wherein $R_1$ is selected from the group consisting of 1,2,4-oxadiazol-5-yl and 1,3,4-thiadiazol-2-yl, both optionally substituted with alkyl of 1 to 3 carbon atoms or alkenyl of 2 to 5 carbon atoms and 1,2,4-oxadiazol-3-yl and 1,3,4-oxadiazol-2-yl, both optionally substituted with alkenyl of 2 to 5 carbon atoms, alkyl of 1 to 3 carbon atoms or alkyl of 1 to 3 carbon atoms substituted with at least one fluorine, $R_2$ and $R_3$ are individually selected from the group consisting of hydrogen, alkyl of 1 to 3 carbon atoms and alkenyl of 2 to 5 carbon atoms or together form alkylene of 3 to 5 carbon atoms, X is selected from the group consisting of —O— and —S—, $R_4$ is alkyl of 1 to 3 carbon atoms and their non-toxic, pharmaceutically acceptable acid addition salts having anxiolytic sedative and hypnotic activity and a novel process and novel intermediates therefor.

17 Claims, No Drawings

2-(1,2,4-OXADIAZOL-5-YL) AND 2-(1,3,4-THIADIAZOL-2-YL-IMIDAZO[1,2-A]PYRIMIDINES

OBJECTS OF THE INVENTION

It is an object of the invention to provide novel imidazo[1,2-a]pyrimidines of formula I and their non-toxic, pharmaceutically acceptable acid addition salts and a novel process and novel intermediates for their preparation.

It is another object of the invention to provide novel anxiolytic, sedative and hypnotic compositions and a novel method of relieving anxiety and insomnia in warm-blooded animals.

These and other objects and advantages of the invention will become obvious from the following detailed description.

THE INVENTION

The novel compounds of the invention are compounds selected from the group consisting of a compound of the formula

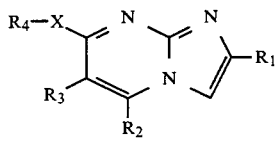

wherein $R_1$ is selected from the group consisting of 1,2,4-oxadiazol-5-yl and 1,3,4-thiadiazol-2-yl, both optionally substituted with alkyl of 1 to 3 carbon atoms or alkenyl of 2 to 5 carbon atoms and 1,2,4-oxadiazol-3-yl and 1,3,4-oxadiazol-2-yl, both optionally substituted with alkenyl of 2 to 5 carbon atoms, alkyl of 1 to 3 carbon atoms or alkyl of 1 to 3 carbon aboms substituted with at least one fluorine, $R_2$ and $R_3$ are individually selected from the group consisting of hydrogen, alkyl of 1 to 3 carbon atoms and alkenyl of 2 to 5 carbon atoms or together form alkylene of 3 to 5 carbon atoms, X is selected from the group consisting of —O— and —S—, $R_4$ is alkyl of 1 to 3carbon atoms and their non-toxic, pharmaceutically acceptable acid addition salts.

Examples of alkyl of 1 to 3 carbon atoms are methyl, ethyl, propyl and isopropyl and when substituted with one or more fluorines are trifluoromethyl, difluoromethyl and fluoromethyl. Examples of alkenyl of 2 to 5 carbon atoms are vinyl, allyl and butenyl. Examples of alkylene of 3 to 5 carbon atoms are propylene, butylene and pentamethylene.

Examples of suitable acids for the formation of non-toxic, pharmaceutically acceptable acid addition salts are mineral acids such as hydrochloric acid, hydrobromic acid, hydroiodic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and aryl sulfonic acids such as benzene sulfonic acid.

Among the preferred compounds of formula I are those wherein $R_1$ is a methyloxadiazolyl, propyloxadiazolyl, 5-trifluoromethyl-1,2,4-oxadiazol-3-yl, 5-trifluoromethyl-1,3,4-oxadiazol-2-yl and methyl thiadiazolyl and especially 3-methyl-1,2,4-oxadiazol-5-yl, 5-methyl-1,2,4-oxadiazol-3-yl, 5-propyl-1,3,4-oxadiazol-2-yl, 5-trifluoromethyl-1,2,4-oxadiazol-3-yl, 5-methyl-1,3,4-oxadiazol-2-yl and 5-methyl-1,3,4-thiadiazol-2-yl and those wherein $R_2$ and $R_3$ are alkyl of 1 to 3 carbon atoms and X is —O—.

Among specific preferred compounds of formula I are those selected from the group consisting of 6-ethyl-7methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2,a]-pyrimidine, 6-ethyl-7-methoxy-5-methyl-2-(5-trifluoromethyl-1,2,4-oxadiazol-3-yl)imidazo[1,2-a]pyrimidine, 6-ethyl-7-methoxy-5-methyl-2-(5-methyl-1,3,4-oxadiazol-2-yl)imidazo[1,2,-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

The compounds of formula I may also exist in the form of solvates such as hydrates and these are included within the scope of the invention.

The novel process for the preparation of a compound of formula I wherein $R_1$ is 1,2,4-oxadiazol-5-yl optionally substituted with alkyl of 1 to 3 carbon atoms or alkenyl of 2 to 5 carbon atoms comprises reacting a compound of the formula

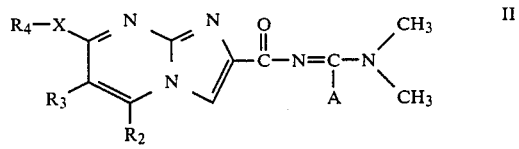

wherein $R_2$, $R_3$, $R_4$ and X have the above definitions and A is selected from the group consisting of hydrogen, alkyl of 1 to 3 carbon atoms and alkenyl of 2 to 5 carbon atoms with hydroxylamine hydrochloride in the presence of a base such as aqueous sodium hydroxide, preferably a stoichiometric amount. The reaction is preferably effected in an organic solvent such as dioxane and in the presence of an acidic organic cosolvent such as glacial acetic acid. Preferably, the reaction mixture is heated to about 90° C. to effect cyclization of the intermediate which need not be isolated.

The compounds of formula II may be prepared in situ by reacting a compound of the formula

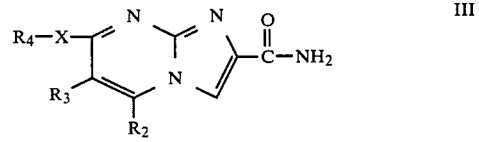

wherein $R_2$, $R_3$, $R_4$ and X have the above definitions with a compound of the formula

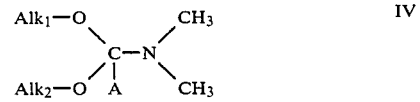

where A has the above definition and $Alk_1$ and $Alk_2$ are alkyl of 1 to 3 carbon atoms. The reaction is preferably effected at elevated temperatures of about 110° C. and the product is then reacted without recovery or purification with hydroxylamine hydrochloride.

The novel process of the invention for the preparation of compounds of formula I wherein $R_1$ is a 1,2,4-oxadiazol-3-yl optionally substituted with alkyl of 1 to 3 carbon atoms, alkyl of 1 to 3 carbon atoms substituted with at least one fluorine and alkenyl of 2 to 5 carbon atoms comprises reacting a compound of the formula

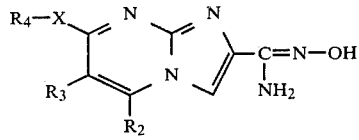

V wherein $R_2$, $R_3$, $R_4$ and X have the above definitions with a reactive derivative of the compound of the formula

    VI wherein D is selected from the group consisting of hydrogen, alkyl of 1 to 3 carbon atoms optionally substituted with at least one fluorine and alkenyl of 2 to 5 carbon atoms.

The reactive derivative of the compound of formula VI may be its acid anhydride, preferably a symmetrical anhydride, or an amido acetal of the formula

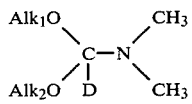    VII wherein D has the above definition and $Alk_1$ and $Alk_2$ are alkyl of 1 to 3 carbon atoms. When the reactive derivative is a strongly dehydrating agent such as trifluoroacetic anhydride, the reaction is effected in the presence of a base such as triethylamine in a low boiling solvent such as dichloromethane at reflux. If the derivative is not strongly dehydrating such as the amido acetal of formula VII or an alkanoic anhydride, the reaction is preferably effected by heating to around 100° C. Other reaction conditions may be used depending on the reactants.

The compounds of formula V may be prepared by reacting a compound of the formula

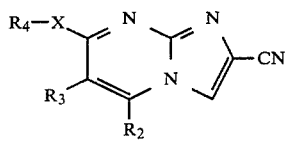    VIII wherein $R_2$, $R_3$, $R_4$ and X have the above definitions with hydroxylamine hydrochloride in the presence of a base such as potassium hydroxide and preferably at reflux in an organic solvent such as ethanol. The product of formula V can be isolated and/or purified or semi-purified by washing before reaction with the reactive derivative of the compound of formula VI.

The novel process of the invention for the preparation of a compound of formula I wherein $R_1$ is 1,3,4-oxadiazol-2-yl optionally sbustituted with alkyl of 1 to 3 carbon atoms, alkenyl of 2 to 5 carbon atoms and alkyl of 1 to 3 carbon atoms substituted with at least one fluorine comprises thermally cyclizing a compound of the formula

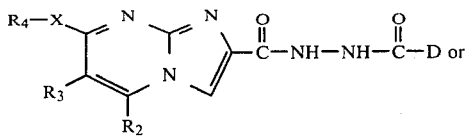

IX

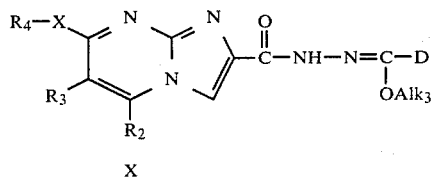

X wherein $R_2$, $R_3$, $R_4$, X and D have the above definitions and $Alk_3$ is alkyl of 1 to 3 carbon atoms.

The compounds of formulae IX and X may be prepared and isolated with optional purification before cyclization or may be made in situ. For example, the compounds of formula IX may be prepared by reacting a compound of the formula

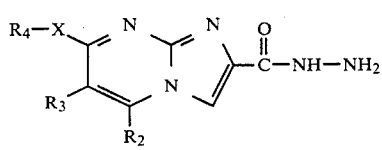    XI wherein $R_2$, $R_3$, $R_4$ and X have the above definitions with a reactive derivative of a compound of formula VI such as the acid anhydrides or less preferably the acid halides such as the acid chlorides. The compounds of formula X may be prepared by reacting a compound of formula XI with a suitable reactive derivative of a compound of formula VI such as its orthoester of the formula

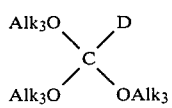    XII wherein D and $Alk_3$ have the above definitions.

When the reactive derivative of the compound of formula VI is a strongly dehydrating agent such as trifluoroacetic anhydride, the compounds of formulae IX or X are prepared in situ in the reaction media which is cyclized without isolation or purification of the intermediate. An excess of the reactive derivative of the compound of formula VI is preferably used in this instance to act as the strongly acidic dehydrating agent for the cyclization step. The cyclization is preferably effected in the presence of a base such as triethylamine in an organic solvent such ad dichloromethane, preferably at 25° to 45° C.

When the reactive derivative of the compound of formula VI is not strongly dehydrating, it is preferred to isolate the compounds of formulae IX or X before cyclization with purification by washing for example. The cyclization step is then preferably effected at an elevated temperature such as 120° C. or more in the optional presence of a strongly acidic dehydrating agent such as polyphosphoric acid or phosphoryl chloride.

The compounds of formula XI may be prepared by reacting a compound of the formula

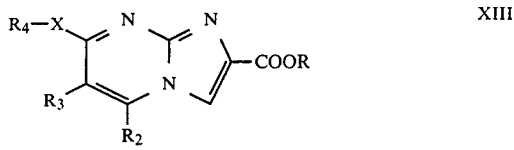

XIII wherein $R_2$, $R_3$, $R_4$ and X have the above definitions and R is an ester group such as alkyl of 1 to 3 carbon atoms like ethyl with hydrazine hydrate, preferably in the presence of an organic solvent such as ethanol, preferably at reflux. The compound of formula XI may be isolated and purified by washing, for example, before further reaction.

The novel process for the preparation of compounds of formula I wherein $R_1$ is a 1,3,4-thiadiazol-2-yl optionally substituted with alkyl of 1 to 3 carbon atoms and alkenyl of 2 to 5 carbon atoms comprises reacting a compound of the formula

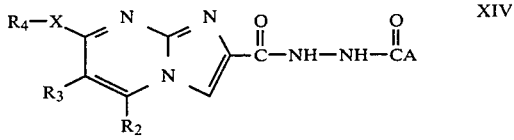

XIV wherein $R_2$, $R_3$, $R_4$ and X have the above definitions and A is hydrogen, alkyl of 1 to 3 carbon atoms or alkenyl of 2 to 5 carbon atoms with Lawesson's reagent which is 2,4-bis-(4-methoxyphenyl)-1,3-dithia-2,4-diphosphetane-2,4-disulfide of the formula

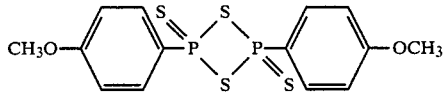

in the presence of an organic solvent such as toluene, preferably at reflux.

The compounds of formula XIV are new and may be prepared by a process analogous to that for the preparation of the compounds of formula IX from compounds of formula XI.

The acid addition salts of the compounds of formula I may be prepared by reacting the compounds of formula I with a stoichiometric amount of a suitable acid in a solvent with or without isolation.

The novel anxiolytic sedative and hypnotic compositions of the invention are comprised of an anxiolytically sedative and hypnotically effective amount of at least one compound of formula I and their non-toxic, pharmaceutically acceptable acid addition salts and an inert pharmaceutical carrier or excipient. The compositions may be in the form of tablets, dragees, capsules, granules, suppositories and injectable solutions or suspensions.

Examples of the excipients are talc, arabic gum, lactose, starch, magnesium stearate, cocoa butter, aqueous and non-aqueous vehicles, fatty substances of animal and vegetable origin, paraffinic derivatives, glycols, various wetting, dispersing and emulsifying agents and preservatives.

The compositions are useful in the treatment of anxiety, chronic anxiety accompanied by agitation, irritability and aggression, anxiety accompanied by insomnia, insomnia and muscular tension and distress.

Among the preferred compositions of the invention are those of formula I wherein $R_1$ is a methyloxadiazolyl, propyloxadiazolyl, 5-trifluoromethyl-1,2,4-oxadiazol-3-yl, 5-trifluoromethyl-1,3,4-oxadiazol-2-yl and methylthiadiazolyl and especially 3-methyl-1,2,4-oxadiazol-3-yl, 5-methyl-1,2,4-oxadiazol-3-yl, 5-propyl-1,3,4-oxadiazol-2-yl, 5-trifluoromethyl-1,2,4-oxadiazol-3-yl, 5-methyl-1,3,4-oxadiazol-2-yl and 5-methyl-1,3,4-thiadiazol-2-yl and those wherein $R_2$ and $R_3$ are alkyl of 1 to 3 carbon atoms and X is —O—.

Among specific preferred compositions of the invention are those wherein the compound of formula I is selected from the group consisting of 6-ethyl-7-methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2-a]pyrimidine, 6-ethyl-7-methoxy-5-methyl-2-(5-trifluoromethyl-1,2,4-oxadiazol-3-yl)imidazo [1,2-a]pyrimidine, 6-ethyl-7-methoxy-5-methyl-2-(5-methyl-1,3,4-oxadiazol-2-yl)imidazo [1,2-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

The novel method of the invention for relieving anxiety in warm-blooded animals, including humans, comprises administering to warm-blooded animals an anxiolytically effective amount of at least one compound of formula I and its non-toxic, pharmaceutically acceptable acid addition salts. The compounds may be orally, rectally or parenterally administered and the usual daily dose is 0.001 to 2.75 mg/kg depending on the specific compound, the condition treated and method of administration.

Some of the compounds of formula III are described in Il Farmaco Ed. Sci., Vol. 35 (1980), p. 654 and those not described therein may be prepared by an analogous process or as described in Example I infra.

The compounds of formula VIII are new and may be prepared by reacting a compound of the formula

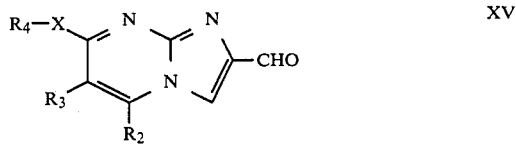

XV wherein $R_2$, $R_3$, $R_4$ and X have the above definitions with hydroxylamine O-sulfonate in the presence of water followed by alkalinization with a base such as sodium hydroxide.

The compounds of formulae XIII and XV have been described in the literature and may be prepared by the process of British Pat. No. 2,128,989.

The intermediates of formulae II, V, VIII, IX, X, XI and XIV are novel and are an object of the invention.

In the following examples there are described several preferred embodiments to illustrate the invention. However, it is to be understood that the invention is not intended to be limited to the specific embodiments.

EXAMPLE 1

(i)

6-Ethyl-7-methoxy-5-methylimidazo[1,2-a]pyrimidine-2-carboxamide

STEP A: 6-Ethyl-7-methoxy-5-methylimidazo[1,2-a]pyrimidine-2-carbonitrile

To a rapidly stirred suspension of 19.84 g of 6-ethyl-7-methoxy-5-methylimidazo[1,2-a]pyrimidine-2-carboxaldehyde in 300 ml of water at room temperature was added all at once a solution of 13.30 g of hydroxylamine-o-sulfonic acid in 250 ml of water. After 40 minutes when the intermediate had precipitated, 8 g of solid sodium hydroxide were added and the intermediate dissolved. After 1 hour when the product had precipitated, the mixture was filtered and the solid was washed with water, dried, then crystallized from ethyl acetate to obtain 16.18 g of 6-ethyl-7-methoxy-5-methylimidazo[1,2-a]pyrimidine-2-carbonitrile (83% yield) as a pale yellow solid melting at 166°–168° C.

Analysis: $C_{11}H_{12}N_4O$ Calculated: %C 61.10, %H 5.60, %N 25.91%; Found: 61.11, 5.65, 25.94.

STEP B: 6-Ethyl-7-methoxy-5-methylimidazo[1,2-a]pyrimidine-2-carboxamide

A suspension of 10.0 g of 6-ethyl-7-methoxy-5-methylimidazo[1,2-a]pyrimidine-2-carbonitrile of Step A and 20.0 g of Amberlite IRA-400 (base form) in 200 ml of water was stirred rapidly at reflux and after 4½ hours, the mixture was cooled. Chloroform was added to dissolve the precipitated product and the two phase mixture was filtered to remove the Amberlite. The layers were separated and the aqueous phase was extracted with chloroform. The combined chloroform layers were dried over $MgSO_4$, filtered and evaporated to dryness. The solid product was crystallized from methanol to obtain 10.5 g (97% yield) of 6-ethyl-7-methoxy-5-methylimidazo[1,2-a]pyrimidine-2-carboxamide as white needles melting at 256°–259° C.

Analysis: $C_{11}H_{14}N_4O_2$ Calculated: %C 56.40, %H 6.02, %N 23.92; Found: 56.27, 6.01, 23.79.

(ii)

6-Ethyl-7-methoxy-5-methyl-2-(3-methyl-1,2,4-oxadiazol-5-yl)imidazo[1,2-a]pyrimidine A mixture of 5.40 g of 6-ethyl-7-methoxy-5-methylimidazo[1,2-a]pyrimidine-2-carboxamide and 11.0 g of dimethylacetamide dimethyl acetal was stirred at 110° C. for 1 hour and then the mixture was evaporated to dryness to give the intermediate as a thick brown oil. The intermediate was treated with 2.24 g of hydroxylamine hydrochloride, 40 ml of dioxane, 40 ml of glacial acetic acid and finally 16.7 ml of 2M sodium hydroxide solution. The resulting solution was heated at 90° C. for 1.75 hours and 60 ml of water were added to the hot mixture which was then cooled. The product crystallized and was crystallized from ethyl acetate to give 3.97 g of 6-ethyl-7-methoxy-5-methyl-2-(3-methyl-1,2,4-oxadiazol-5-yl)imidazo[1,2-a]pyrimidine (63% yield) as white micro needles melting at 204°–205° C.

EXAMPLE 2

6-Ethyl-7-methoxy-5-methyl-2-(5-methyl-1,2,4-oxadiazol-3-yl)imidazo[1,2-a]pyrimidine STEP A: 6-Ethyl-N-hydroxy-7-methoxy-5-methylimidazo[1,2-a]pyrimidine-2-carboxamidine A suspension of 8.0 g of 6-ethyl-7-methoxy-5-methylimidazo [1,2-a]pyrimidine-2-carbonitrile, 2.82 g of hydroxylamine hydrochloride and 2.28 g of potassium hydroxide in 100 ml of ethanol was refluxed with stirring for 2 hours and the mixture was cooled. The precipitated product was filtered, suspended in water with stirring for 15 minutes, filtered, then washed with water and ether and dried under vacuum to give 7.96 g of 6-ethyl-N-hydroxy-7-methoxy-5-methylimidazo[1,2-a]pyrimidine-2-carboxamidine (86% yield) melting at 249°–250° C.

STEP B: 6-Ethyl-7-methoxy-5-methyl-2-(5-methyl-1,2,4-oxadiazol-3-yl)imidazo[1,2-a]pyrimidine A mixture of 1.70 g of 6-ethyl-N-hydroxy-7-methoxy-5-methylimidazo[1,2-a]pyrimidine-2-carboxamidine and 3.5 ml of dimethylacetamide dimethyl acetal was heated at 100° C. for 15 minutes and the resulting mixture was evaporated to dryness and purified by flash chromatography. The resulting solid was crystallized from aqueous methanol to give 1.76 g of 6-ethyl-7-methoxy-5-methyl-2-(5-methyl-1,2,4-oxadiazol-3-yl)imidazol[1,2-a]pyrimidine (95% yield) as a white crystalline solid melting at 176°–177° C.

EXAMPLE 3

6-Ethyl-7-methoxy-5-methyl-2-(5-propyl-1,3,4-oxadiazol-2-yl)imidazo[1,2-a]pyrimidine STEP A: 6-Ethyl-7-methoxy-5-methylimidazo[1,2-a]pyrimidine-2-carbohydrazide A solution of 10.0 g of ethyl 6-ethyl-7-methoxy-5-methylimidazo[1,2-a]pyrimidine-2-carboxylate (published UK Patent Application No. 2,128,989) and 20 ml of hydrazine hydrate in 150 ml of ethanol was refluxed for 4 hours. Most of the ethanol was evaporated and 100 ml of water were added. The resulting precipitate was filtered, washed with water, then ether and dried under vacuum over $P_2O_5$ to obtain 8.15 g of 6-ethyl-7-methoxy-5-methylimidazo[1,2-a]pyrimidine-2-carbohydrazide (86% yield) as an off-white solid.

STEP B: 2-Butyryl-(6-ethyl-7-methoxy-5-methylimidazo[1,2-a]pyrimidin-2-yl)carbohydrazide A solution of 2.00 g of the hydrazide of Step A, 1.7 ml of triethylamine and 1.96 of butyric anhydride in 200 ml of ethanol was refluxed for 2 hours, then cooled in ice and the resulting precipitate was filtered, washed with ethanol, then ether and dried under vacuum to obtain 2.3 g of 2-butyryl-(6-ethyl-7-methoxy-5-methylimidazo[1,2-a]pyrimidin-2-yl)carbohydrazide (90% yield) as a white solid.

STEP C: 6-Ethyl-7-methoxy-5-methyl-2-(5-propyl-1,3,4-oxadiazol-2-yl)imidazo[1,2-a]pyrimidine A mixture of 2.3 g of 2-butyryl-(6-ethyl-7-methoxy-5-methylimidazo[1,2-a]pyrimidin-2-yl)carbohydrazide of Step B and 50 g of polyphosphoric acid was stirred at 120° C. for 1 hour. The mixture was then cooled, poured into ice-water, neutralized with sodium carbonate and extracted 3 times with chloroform. The chloroform layer was dried over $MgSO_4$, filtered and evaporated to dryness and the resulting product was purified by flash chromatography followed by crystallization from ethylacetate to obtain 1.62 g of 6-ethyl-7-methoxy- 5-methyl-2-(5-propyl-1,3,4-oxadiazol-2-yl)imidazo[1,2-a]pyrimidine (75% yield) as a white crystalline solid melting at 180°–181.5° C. This cyclization was also carried out using phosphoryl chloride, although yields were lower.

EXAMPLE 4

6-Ethyl-7-methoxy-5-methyl-2-(5-methyl-1,3,4-oxadiazol-2-yl)imidazo[1,2-a]pyrimidine Using the procedure of Steps B and C of Example 3, 6-ethyl-7-methoxy-5-methylimidazo[1,2-a]pyrimidine-2-carbohydrazide and acetic anhydride were reacted to obtain a 34% yield of 6-ethyl-7-methoxy-5-methyl-2-(5-methyl-1,3,4-oxadiazol-2-yl)imidazo[1,2-a]pyrimidine.

EXAMPLE 5

6-Ethyl-7-methoxy-5-methyl-2-(5-methyl-1,3,4-thiadiazol-2-yl)imidazol[1,2-a]pyrimidine A suspension of 2.67 g of 2-acetyl-(6-ethyl-7-methoxy-5-methylimidazo[1,2-a]pyrimidine-2-yl)carbohydrazide (prepared analogously to Steps A and B of Example 3 above, acetic anhydride in place of butyric anhydride) and 4.70 g of Lawesson's Reagent in 90 ml of dry toluene was refluxed for 45 minutes and the mixture was then cooled and partitioned between 100 ml of chloroform and 100 ml of water. The organic layer was washed with 5% sodium bicarbonate, dilute sodium hydroxide solution and saturated sodium chloride, then dried over MgSO4, filtered and evaporated to dryness. The resulting product was purified by flash chromatography followed by crystallization from ethyl acetate to obtain 0.90 g of 6-ethyl-7-methoxy-5-methyl-2-(5-methyl-1,3,4-thiadiazol-2-yl)imidazo[1,2-a]pyrimidine (as a 0.25 hydrate) (34% yield) as a buff powder melting at 210.5°–212° C.

EXAMPLE 6

6-Ethyl-7-methoxy-5-methyl-2-(5-trifluoromethyl-1,3,4-oxadiazol-2-yl)imidazo[1,2-a]pyrimidine To a solution of 1.20 g (4.81 mmol) of 6-ethyl-7-methoxy-5-methylimidazo[1,2-a]pyrimidine-2-carbohydrazide and 0.8 ml of triethylamine in 30 ml of dry dichloromethane under stirring at room temperature was added dropwise 1.7 ml of trifluoroacetic anhydride. The mixture was heated at 45° C. for 30 minutes, then cooled and 3 times washed with water, dried over MgSO4, filtered and the solvent evaporated. The product was crystallized from ethyl acetate to give 1.50 g of 6-ethyl-7-methoxy-5-methyl-2-(5-trifluoromethyl-1,3,4-oxadiazol-2-yl)imidazo[1,2-a]pyrimidine (82% yield) as a fluffy white solid melting at 210°–211° C.

EXAMPLE 7

6-Ethyl-7-methoxy-5-methyl-2-(5-trifluoromethyl-1,2,4-oxadiazol-3-yl)imidazo[1,2-a]pyrimidine Using the procedure of Example 6, 6-ethyl-N-hydroxy-7-methoxy-5-methylimidazo[1,2-a]pyrimidine-2-carboxamidine was reacted to obtain a 95% yield of 6-ethyl-7-methoxy-5-methyl-2-(5-trifluoromethyl-1,2,4-oxadiazol-3-yl)imidazo[1,2-a]pyrimidine melting at 197°–200° C.

EXAMPLE 8

6-Ethyl-7-methoxy-5-methyl-2-(1,3,4-oxadiazol-2-yl)imidazo[1,2-a]pyrimidine

A suspension of 2.50 g of 6-ethyl-7-methoxy-5-methylimidazo[1,2-a]pyrimidine-2-carbohydrazide in 20 ml of triethyl orthoformate was heated at 125° C. for 6 hours and the mixture was cooled. The precipitate was filtered, washed with ether, and dried to obtain 2.88 g (94% yield) of ethyl N-[(6-ethyl-7-methoxy-5-methylimidazo[1,2-a]pyrimidine-2-yl)carboxamido]formimidate.

A suspension of 1.88 g of the said imidate in 50 g of polyphosphoric acid was stirred at 120° C. for 1 hour. The mixture was cooled, poured into ice-water, neutralized to pH 7 with solid sodium carbonate. The mixture was extracted 3 times with chloroform and the combined chloroform layer was dried over MgSO4, filtered and evaporated. The product was purified by flash chromatography, then crystallized from ethyl acetate to obtain 1.10 g (69% yield) of 6-ethyl-7-methoxy-5-methyl-2-(1,3,4-oxadiazol-2-yl)imidazo[1,2-a]pyrimidine as a white crystalline solid melting at 198.5°–199° C.

EXAMPLE 9

6-Ethyl-2-(5-ethyl-1,3,4-oxadiazol-2-yl)-7-methoxy-5-methylimidazo[1,2-a]pyrimidine Using the procedure of Steps B and C of Example 3, propionic anhydride was reacted in place of butyric anhydride to obtain a 46% yield of 6-ethyl-2-(5-ethyl-1,3,4-oxadiazol-2-yl)-7-methoxy-5-methylimidazo[1,2-a]pyrimidine melting at 170°–172° C.

Using a method analogous to that described in Steps B and C of Example 3, but starting from the appropriate hydrazide of formula XI and acetic anhydride, the compounds of Examples 10 to 13 were prepared:

EXAMPLE 10

6-Ethyl-5-methyl-2-(5-methyl-1,3,4-oxadiazol-2-yl)-7-methylthioimidazo[1,2-a]pyrimidine

EXAMPLE 11

6,7,8,9-Tetrahydro-5-methoxy-2-(5-methyl-1,3,4-oxadiazol-2-yl)imidazo[1,2-a]quinazoline

EXAMPLE 12

7-Methoxy-5-methyl-2-(5-methyl-1,3,4-oxadiazol-2-yl)-6-propylimidazo[1,2-a]pyrimidine

EXAMPLE 13

7-Methoxy-5-methyl-2-(5-methyl-1,3,4-oxadiazol-2yl)-6-(1-propenyl)imidazo[1,2-a]pyrimidine Using the procedure of Example 2, but starting from the appropriate carbonitrile of formula VIII, the compounds of Examples 14 to 17 were prepared:

EXAMPLE 14

7-Methoxy-5-methyl-2-(5-methyl-1,2,4-oxadiazol-3-yl)-6-propylimidazo[1,2-a]pyrimidine

EXAMPLE 15

6-Ethyl-5-methyl-2-(5-methyl-1,2,4-oxadiazol-3-yl)-7-methylthioimidazo[1,2-a]pyrimidine

EXAMPLE 16

6-Allyl-7-methoxy-2-(5-methyl-1,2,4-oxadiazol-3-yl)-5-methylimidazo[1,2-a]pyrimidine

EXAMPLE 17

6,7,8,9-Tetrahydro-5-methoxy-2-(5-methyl-1,2,4-oxadiazol-3-yl)imidazo[1,2-a]quinazoline

EXAMPLE 18

6-Allyl-7-methoxy-5-methyl-2-(5-methyl-1,3,4-oxadiazol-2-yl)imidazo[1,2-a]pyrimidine A mixture of 3.58 g of 6-allyl-7-methoxy-5-methylimidazo[1,2-a]pyrimidine-2-carbohydrazide and 25 cm3 of triethyl orthoacetate was heated at 150°–180° C. for 16 hours. The mixture was then cooled and evaporated to dryness and the resulting crude product purified by flash chromatography to obtain 1.47 g of 6-allyl-7-methoxy-5-methyl-2-(5-methyl-1,3,4-oxadiazol-2-yl)imidazo[1,2-a]pyrimidine.

The results are reported in the following Tables

TABLE II $$(I)$$

(Structure: pyrimidine with R_4-X at 4-position, R_3 at 5, R_2 at 6, R_1 at 2)

| Example | R_1 | R_2 | R_3 | R_4 | X | Yield (%) | IR(KBr) cm$^{-1}$ | Mpt °C. | Formula | M. wt. | Theory/Found C | H | N | S/F |
|---|---|---|---|---|---|---|---|---|---|---|---|---|---|---|
| 1(ii) | isoxazol-3-yl (5-Me) | Me | Et | Me | O | 63 | 3145,1638,1613 | 204–205 | $C_{13}H_{15}N_5O_2$ | 273.3 | 57.13 57.14 | 5.53 5.53 | 25.62 25.58 | |
| 2 | oxazol-2-yl (5-Me) | Me | Et | Me | O | 95 | 3170,1638,1603 | 176–177 | $C_{13}H_{15}N_5O_2$ | 273.3 | 57.13 57.08 | 5.53 5.59 | 25.62 25.64 | |
| 3 | oxazol-2-yl (5-nPr) | Me | Et | Me | O | 75 | 3120,2960,2940,2870, 1635,1608 | 181–181.5 | $C_{15}H_{19}N_5O_2$ | 301.2 | 59.79 60.07 | 6.35 6.33 | 23.24 23.26 | |
| 4 | oxazol-2-yl (5-Me) | Me | Et | Me | O | 34 | 3140,2980,2955,1630 | 193.5–195 | $C_{13}H_{15}N_5O_2$ | 273.3 | 57.13 57.35 | 5.53 5.50 | 25.62 25.59 | |
| 5 | thiazol-2-yl (5-Me) | Me | Et | Me | O | 34 | 3102,2960,2925,2875, 1635 | 210.5–212 | $C_{13}H_{15}N_5OS + \frac{1}{2}H_2O$ | 293.8 | 53.14 53.31 | 5.32 5.15 | 23.83 23.79 | 10.91 11.19 |
| 6 | oxazol-2-yl (5-CF_3) | Me | Et | Me | O | 82 | 3125,2975,2950,1640, 1605 | 210–211 | $C_{13}H_{12}N_5O_2F_3$ | 327.3 | 47.71 47.76 | 3.70 3.73 | 21.40 21.44 | 17.42 17.44 |
| 7 | isoxazol-3-yl (5-CF_3) | Me | Et | Me | O | 95 | 3150,2990,2950,1635, 1600 | 197–200 | $C_{13}H_{12}N_5O_2F_3$ | 327.3 | 47.71 47.79 | 3.70 3.78 | 21.40 21.39 | 17.42 17.25 |

TABLE II-continued (I)

| Example | R₁ | R₂ | R₃ | R₄ | X | Yield (%) | IR(KBr) cm⁻¹ | Mpt °C. | Formula | M. wt. | Theory/Found C | H | N | S/F |
|---|---|---|---|---|---|---|---|---|---|---|---|---|---|---|
| 8 | (N-N ring, H) | Me | Et | Me | O | 69 | 3120,2970,2945,1635, 1605 | 198.5–199 | C₁₂H₁₃N₅O₂ | 259.3 | 55.59 | 5.05 | 27.01 | |
| 9 | (N-N ring, Et) | Me | Et | Me | O | 46 | 3150,2978,2950,1625 | 170–172 | C₁₄H₁₇N₅O₂ | 287.3 | 58.53 | 5.97 | 24.37 | |
| 10 | (N-N ring, Me) | Me | Et | Me | S | 81 | 3160,2960,2930,1615 | 175–175.5 | C₁₃H₁₅N₅OS | 289.35 | 53.96 / 53.96 | 5.34 / 5.28 | 24.20 / 24.21 | 11.08 / 11.08 |
| 11 | (N-N ring, Me) | Me | —CH₂CH₂CH₂CH₂— | Me | O | 77 | 3175,2990,2940,2880, 1640,1627 | 222–226 | C₁₄H₁₅N₅O₂ | 285.31 | 58.94 / 58.92 | 5.30 / 5.34 | 24.55 / 24.60 | |
| 12 | (N-N ring, Me) | Me | Pr | Me | O | 93 | 3125,3100,2950,2930, 2870,1635,1610 | 219–220 | C₁₄H₁₇N₅O₂ | 287.33 | 58.53 / 58.56 | 5.97 / 5.99 | 24.37 / 24.43 | |
| 13 | (N-N ring, Me) | Me | CH₃—CH=CH— | Me | O | 48 | 2955,1630,1615 | 202–210 | C₁₄H₁₅N₅O₂ | 285.31 | 58.94 / 58.64 | 5.30 / 5.36 | 24.55 / 24.15 | |

TABLE II-continued (I) structure: R4—X, R3, R2, R1 on pyrimidine with N,N

| Example | R1 | R2 | R3 | R4 | X | Yield (%) | IR(KBr) cm⁻¹ | Mpt °C. | Formula | M. wt. | Theory/Found C | H | N | S/F |
|---|---|---|---|---|---|---|---|---|---|---|---|---|---|---|
| 14 | oxazole-Me | Me | Pr | Me | O | 87 | 33155,2950,2870,1636, 1600 | 185-185.5 | $C_{14}H_{17}N_5O_2$ | 287.33 | 58.53/58.59 | 5.97/5.99 | 24.37/24.47 | |
| 15 | oxazole-Me | Me | Et | Me | S | 89 | 2960,2930,1613 | 209-210 | $C_{13}H_{15}N_5OS$ | 289.30 | 53.96/53.91 | 5.23/5.24 | 24.20/24.23 | 11.0/11.0 |
| 16 | oxazole-Me | Me | allyl | Me | O | 80 | 3000,2950,1635,1600 | 147-150 | $C_{14}H_{15}N_5O_2 + \tfrac{2}{3}H_2O$ | 297.32 | 56.55/56.69 | 5.54/5.26 | 23.55/23.67 | |
| 17 | oxazole-Me | —CH₂CH₂CH₂CH₂— | | Me | O | 75 | 2945,2880,1643,1600 | 218-222 | $C_{14}H_{15}N_5O_2$ | 285.31 | 58.94/58.95 | 5.30/5.35 | 24.55/24.55 | |
| 18 | isoxazole-Me | Me | allyl | Me | O | 34 | 3122,3102,2950,2925, 1635,1610 | 186-188 | $C_{14}H_{15}N_5O_2$ | 285.31 | 58.94/58.88 | 5.30/5.35 | 24.55/24.46 | |

EXAMPLE 19

Tablets were prepared containing 20 mg of the compound of Example 1(ii) or 4 and sufficient excipient of lactose, starch, talc and magnesium stearate for a final tablet weight of 150 mg.

PHARMACOLOGICAL DATA

A. Anxiolytic Activity

Screening for anxiolytic activity was carried out by modification of the conflict method of Geller et al (Psychopharmacologia, 1960, Vol. 1, Page 482). The values given in Table I are the minimum effective doses at which there was an observed increase in shocks above control (MED mg/kg p.o.).

TABLE I

| Example | GELLER CONFLICT (Med mg/kg p.o.) |
|---|---|
| 1 | 5 |
| 2 | 5 |
| 3 | 10-50 |
| 4 | 2 |
| 5 | 10 |
| 6 | 10-50 |
| 7 | 2 |
| 8 | >50 |
| 9 | 50 |
| 10 | 5 |
| 11 | 50 |
| 12 | 10 |
| 13 | 50 |
| 14 | 5 |
| 15 | 2 |
| 16 | 10 |
| 17 | 5 |
| 18 | 10 |

Various modifications of the products and methods of the invention may be made without departing from the spirit or scope thereof and it is to be understood that the invention is intended to be limited only as defined in the appended claims.

What we claim is:

1. A compound selected from the group consisting of a compound of the formula

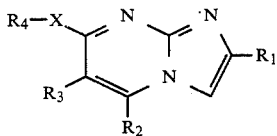

wherein $R_1$ is selected from the group consisting of 1,2,4-oxadiazol-5-yl and 1,3,4-thiadiazol-2-yl, both optionally substituted with alkyl of 1 to 3 carbon atoms or alkenyl of 2 to 5 carbon atoms and 1,2,4-oxadiazol-3-yl and 1,3,4-oxadiazol-2-yl, both optionally substituted with alkenyl of 2 to 5 carbon atoms, alkyl of 1 to 3 carbon atoms or alkyl of 1 to 3 carbon atoms substituted with at least one fluorine, $R_2$ and $R_3$ are individually selected from the group consisting of hydrogen, alkyl of 1 to 3 carbon atoms and alkenyl of 2 to 5 carbon atoms or together form alkylene of 3 to 5 carbon atoms, X is selected from the group consisting of —O— and —S—, $R_4$ is alkyl of 1 to 3 carbon atoms and their non-toxic pharmaceutically acceptable acid addition salts.

2. A compound of claim 1 wherein $R_1$ is selected from the group consisting of methyloxadiazolyl, propyloxadiazolyl, 5-trifluoromethyl-1,2,4-oxadiazol-3-yl, 5-trifluoromethyl-1,3,4-oxadiazol-2-yl and methylthiadiazolyl.

3. A compound of claim 1 wherein $R_1$ is selected from the group consisting of 3-methyl-1,2,4-oxadiazol-5-yl, 5-methyl-1,2,4-oxadiazol-3-yl, 5-propyl-1,3,4-oxadiazol-2-yl, 5-trifluoromethyl-1,2,4-oxadiazol-3-yl, 5-methyl-1,3,4-oxadiazol-2-yl and 5-methyl-1,3,4-thiadiazol-2-yl.

4. A compound of claim 1 wherein X is —O— and $R_2$ and $R_3$ are alkyl 1 to 3 carbon atoms.

5. A compound of claim 1 selected from the group consisting of 6-ethyl-7-methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2-a]pyrimidine, 6-ethyl-7-methoxy-5-methyl-2-(5-trifluoromethyl-1,2,4-oxadiazol-3-yl)imidazo[1,2-a]pyrimidine, 6 ethyl-7-methoxy-5-methyl-2-(5-methyl-1,3,4-oxadiazol-2-yl)imidazo[1,2-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

6. A anxiolytic composition comprising an anxiolytically effective amount of at least one compound of claim 1 and an inert pharmaceutical carrier.

7. A composition of claim 6 wherein $R_1$ is selected from the group consisting of methyl oxadiazolyl, propyloxadiazolyl, 5-trifluoromethyl-1,2,4-oxadiazol-3-yl, 5-trifluoromethyl-1,3,4-oxadiazol-2-yl and methylthiadiazolyl.

8. A composition of claim 6 wherein $R_1$ is selected from the group consisting of 3-methyl-1,2,4-oxadiazol-5-yl, 5-methyl-1,2,4-oxadiazol-3-yl, 5-propyl-1,3,4-oxadiazol-2-yl, 5-trifluoromethyl-1,2,4-oxadiazol-3-yl, 5-methyl-1,3,4-oxadiazol-2-yl and 5-methyl-1,3,4-thiadiazol-2-yl.

9. A composition of claim 6 wherein X is —O— and $R_2$ and $R_3$ are alkyl of 1 to 3 carbon atoms.

10. A composition of claim 6 wherein the active compound is selected from the group consisting of 6-ethyl-7-methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2-a]pyrimidine, 6-ethyl-7-methoxy-5-methyl-2-(5-trifluoromethyl-1,2,4-oxadiazol-3-yl)imidazo[1,2,a]-pyrimidine, 6-ethyl-7-methoxy-5-methyl-2-(5-methyl-1,3,4-oxadiazol-2-yl)imidazo[1,2-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

11. A method of relieving anxiety in warm-blooded animals comprising administering to warm-blooded animals an anxiolytically effective amount of at least one compound of claim 1.

12. A method of claim 11 wherein $R_1$ is selected from the group consisting of methyloxadiazolyl, propyloxadiazolyl, 5-trifluoromethyl-1,2,4-oxadiazol-3-yl, 5-trifluoromethyl-1,3,4-oxadiazol-2-yl and methylthiadiazolyl.

13. A method of claim 11 wherein $R_1$ is selected from the group consisting of 3-methyl-1,2,4-oxadiazol-5-yl, 5-methyl-1,2,4-oxadiazol-3-yl, 5-propyl-1,3,4-oxadiazol-2-yl, 5-trifluoromethyl-1,2,4-oxadiazol-3-yl, 5-methyl-1,3,4-oxadiazol-2-yl and 5-methyl-1,3,4-thiadiazol-2-yl.

14. A method of claim 11 wherein X is —O— and $R_2$ and $R_3$ are alkyl of 1 to 3 carbon atoms.

15. A method of claim 11 wherein the active compound is selected from the group consisting of 6-ethyl-7-methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2-a]pyrimidine, 6-ethyl-7-methoxy-5-methyl-2-(5-trifluoromethyl-1,2,4-oxadiazol-3-yl)imidazo[1,2-a]pyrimidine, 6-ethyl-7-methoxy-5-methyl-2-(5-methyl-1,3,4-oxadiazol-2-yl)imidazo[1,2-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]-pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

16. A method of relieving insomnia in warm-blooded animals comprising administering to warm-blooded animals a sedative and hypnotically effective amount of at least one compound of claim 1.

17. A method of claim 16 wherein the active compound is selected from the group consisting of 6-ethyl-7-methoxy-5-methyl-2-(3-methyl-1,2,4-oxadiazol-5-yl)imidazo[1,2-a]pyrimidine, 6-ethyl-7-methoxy-5-methyl-2-(5-methyl-1,2,4-oxadiazol-3-yl)imidazo[1,2-a]pyrimidine, 6-ethyl-7-methoxy-5-methyl-2-(5-trifluoromethyl-1,2,4-oxadiazol-3-yl)imidazo[1,2,a]-pyrimidine, 6-ethyl-7-methoxy-5-methyl-2-(5-methyl-1,3,4-oxadiazol-2-yl)imidazo[1,2-a]pyrimidine, 6-ethyl-5-methyl-2-(5-methyl-1,3,4-oxadiazol-2-yl)-7-methylthioimidazo[1,2-a]pyrimidine, 7-methoxy-5-methyl-2-(5-methyl-1,2,4-oxadiazol-3-yl)-6-propylimidazo[1,2-a]pyrimidine, 6-ethyl-5-methyl-2-(5-methyl-1,2,4-oxadiazol-3-yl)-7-methylthioimidazo[1,2-a]pyrimidine and 6,7,8,9-tetrahydro-5-methoxy-2-(5-methyl-1,2,4-oxadiazol-3-yl)imidazo[1,2-a]quinazoline and their non-toxic, pharmaceutically acceptable acid addition salts.

* * * * *